United States Patent [19]
Raviv et al.

[11] Patent Number: 6,045,514
[45] Date of Patent: Apr. 4, 2000

[54] METHOD OF MEASURING BREATHING RESISTANCE OF A SLEEPING SUBJECT

[75] Inventors: Gil Raviv, Northbrook; Charles Z. Weingarten, Wilmette, both of Ill.

[73] Assignee: SNAP Laboratories, L.L.C., Glenview, Ill.

[21] Appl. No.: 08/876,444

[22] Filed: Jun. 16, 1997

Related U.S. Application Data

[63] Continuation-in-part of application No. 08/362,813, Dec. 22, 1994, Pat. No. 5,782,240.

[51] Int. Cl.[7] .................................................. A61B 5/103
[52] U.S. Cl. ........................................... 600/529; 600/587
[58] Field of Search ..................... 600/529, 534, 600/586, 587, 484

[56] References Cited

U.S. PATENT DOCUMENTS

| | | | |
|---|---|---|---|
| 4,365,636 | 12/1982 | Barker | 600/529 |
| 4,777,962 | 10/1988 | Watson et al. | 600/529 |
| 5,275,159 | 1/1994 | Griebel | 600/324 |
| 5,617,846 | 4/1997 | Graetz et al. | 128/204.21 |

Primary Examiner—Cary O'Connor
Assistant Examiner—Pamela L. Wingood
Attorney, Agent, or Firm—Welsh & Katz, Ltd.

[57] ABSTRACT

The invention provides a method of determining a breathing resistance index of a sleeping subject from a set of respiratory sounds. The method includes the steps of selecting a first set of respiratory events of the set of respiratory sounds and manually determining a classification content of the first set of respiratory events. The method further includes extrapolating the classification content of the first set of respiratory events to an at least second set of respiratory events and determining a breathing resistance index based upon the classification content of the at least second set of respiratory events.

16 Claims, 10 Drawing Sheets

Microfiche Appendix Included
(1 Microfiche, 26 Pages)

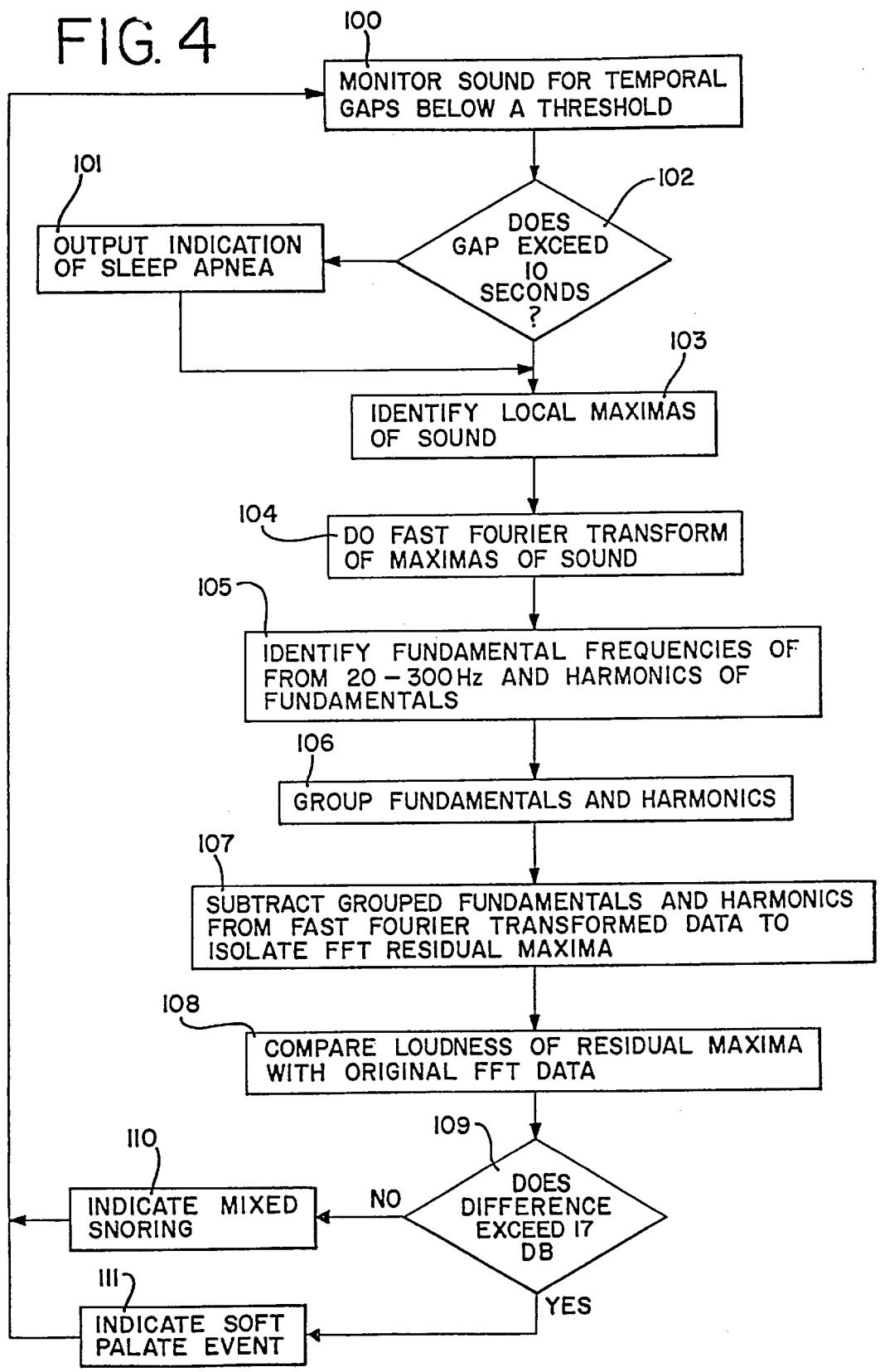

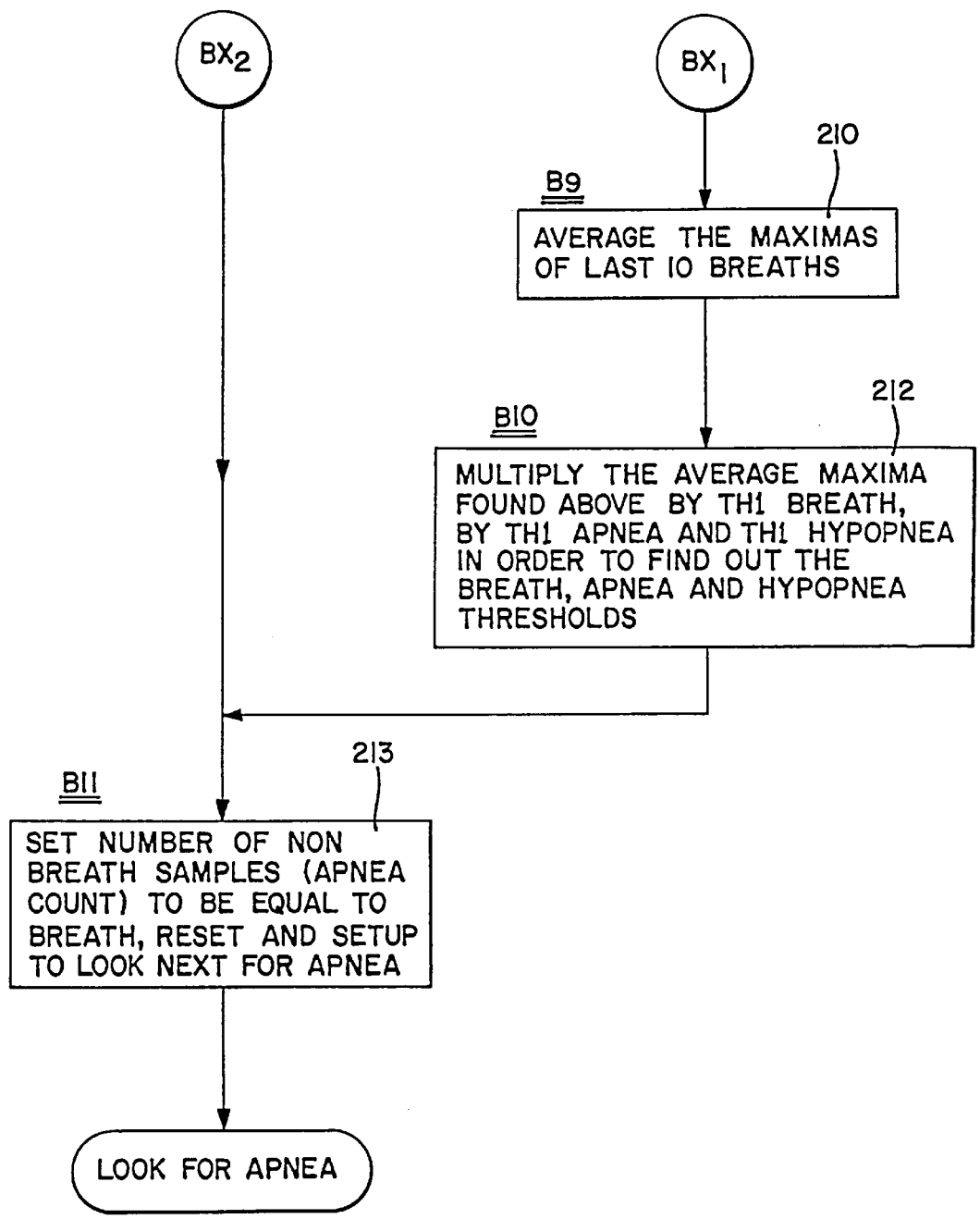

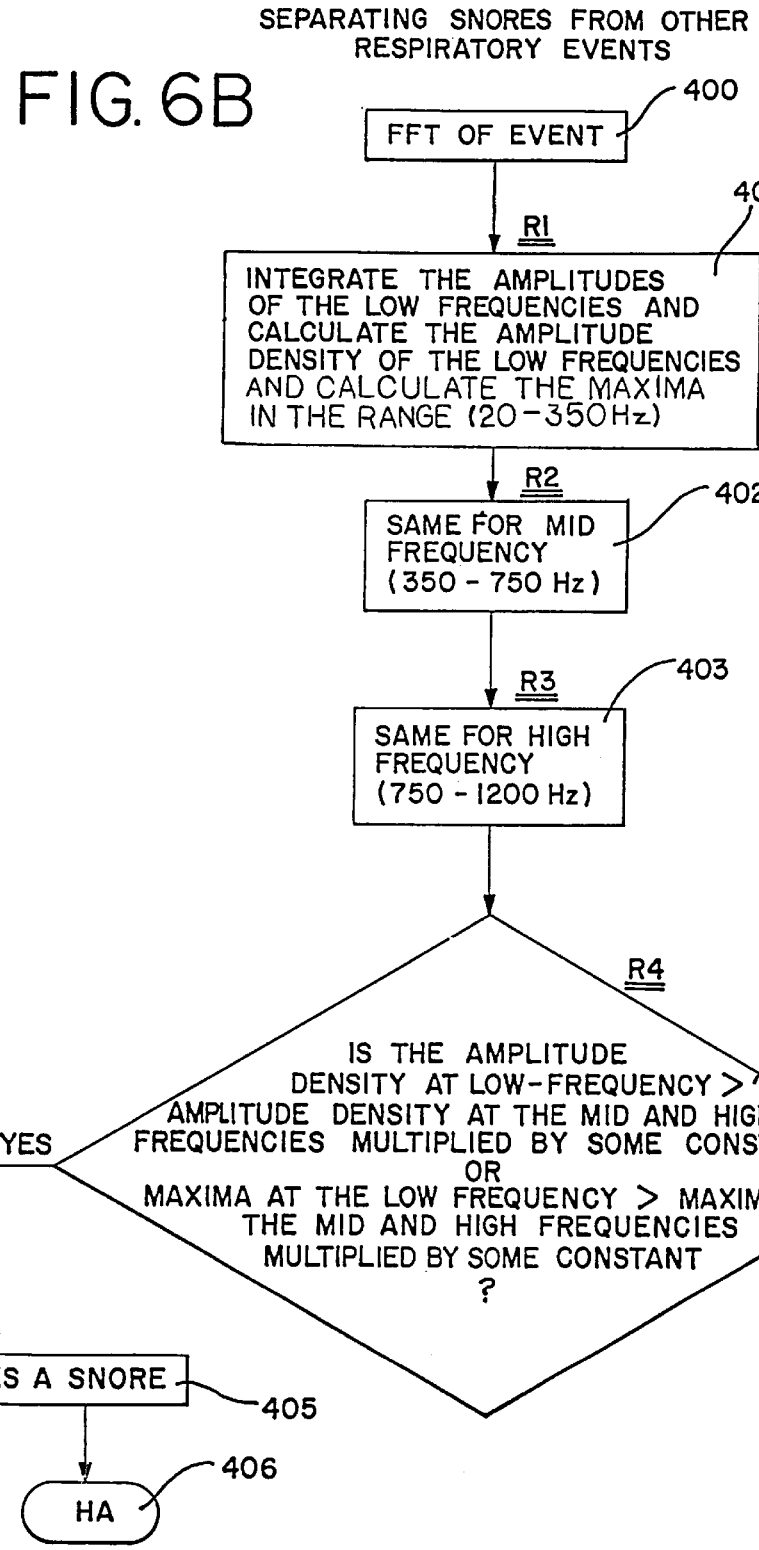

METHOD OF MEASURING BREATHING RESISTANCE OF A SLEEPING SUBJECT

This is a CIP of Ser. No. 08/362,813 filed Dec. 12, 1994 now U.S. Pat. No. 5,782,240.

This document incorporates a Microfiche Appendix comprising 26 frames.

The present invention relates to sleep disorders and in particular to methods and apparatus for measuring breathing resistance of a sleeping subject.

BACKGROUND OF THE INVENTION

An awareness of the risks of sleep disorders in recent years has prompted a number of advances associated with sleep apnea and snoring. Sleep apnea is a known factor associated with heart problems.

Sleep apnea is generally regarded as an interruption in the breathing pattern of a sleeping subject. Interruptions of a breathing pattern may be spontaneous or may result from a breathing obstruction such as a sleeping subject's tongue blocking the airway or from partial or complete upper airway occlusion where the upper airway collapses, particularly under the reduced pressure generated by inhalation. Obstructive sleep apnea may result in lowered arterial blood oxygen levels and poor quality of sleep.

It is estimated that there are more than 40 million chronic snorers in the United States. Snoring is often a factor associated with sleep apnea. In addition to heart problems, sleeping disorders degrade the quality of rest for a person with the sleeping disorder as well as other people, such as a spouse, sharing the sleeping quarters.

Prior art efforts to provide data relative to sleep disorders have included the Sleep Apnea Monitor of U.S. Pat. No. 4,802,485. U.S. Pat. No. 4,804,485 provides a method of monitoring for sleep apnea that includes a number of sensors (blood-oxygen sensor, snoring sensor and head position sensor) mounted to headgear of a monitored subject. The sensors are, in turn, interconnected with a data logger for recording and subsequent analysis by a doctor or technician.

Other patents, such as U.S. Pat. No. 4,982,738, have included additional sensors for recording the time intervals between snoring events. Such advances have improved the content of the data recorded for later analysis by trained personnel.

Another advance, such as U.S. Pat. No. 5,275,159, have used a computer in conjunction with a data logger to improve the presentation of recorded data. The data logged under the invention of U.S. Pat. No. 5,274,159 could be presented under any of three possible formats: (1) as a graph of sensor value versus time; (2) as histograms and tables; and (3) as episodes per hour of a selected parameter.

While the prior art has offered a number of improvements in the technology associated with presenting recorded data, the final diagnosis of the source of the sleep disorder still lies with the attending physician.

The most common surgical procedure used by physicians for correcting sleep disorders such as apnea or snoring is uvulopalatopharnygoplasty ("UPPP"). Other procedures often used include adenoidectomy, tonsillectomy, septoplasty, turbinectomy, and polypectomy. In some cases physicians even perform surgery of the hypopharynx and tongue.

In the case of snoring, if the generation site of the snoring is below the plane of the uvula, then surgery becomes very complicated and, often, impractical. Also, although there is no definitive method for identifying sources of snoring, statistics show that UPPP reduces apnea 50% of the time and snoring 75–80% of the time. Because of the importance of the proper diagnosis of sleep disorders, a need exists for a simple and convenient method of determining the sources and types of sleep disorders that is not completely dependent upon the judgment and experience of an attending physician. It would be further advantageous to be able to easily identify the source of snoring to permit evaluation of the probability of success of the various surgical options.

Further, because of the risks associated with breathing obstructions, a need exists for a method of generating in index of breathing difficulty. Such index should transcend the known categories of symptoms to give a physician an indication of the types of risks associated with the level of breathing difficulty (e.g., heart problems, stroke, etc.)

SUMMARY OF THE INVENTION

In summary, the invention provides a method of determining a breathing resistance index of a sleeping subject from a set of respiratory sounds. The method includes the steps of selecting a first set of respiratory events of the set of respiratory sounds and manually determining a classification content of the first set of respiratory events. The method further includes extrapolating the classification content of the first set of respiratory events to an at least second set of respiratory events and determining a breathing resistance index based upon the classification content of the at least second set of respiratory events.

BRIEF DESCRIPTION OF THE DRAWINGS

FIG. 4 is a flow chart of data analysis in accordance with the invention.

FIGS. 5A and 5B are a flow chart for breath detection in accordance with the invention.

FIGS. 6A–6F are a flow chart of apnea/snoring analysis in accordance with the invention.

BRIEF DESCRIPTION OF MICROFICHE APPENDIX

Figure 1:
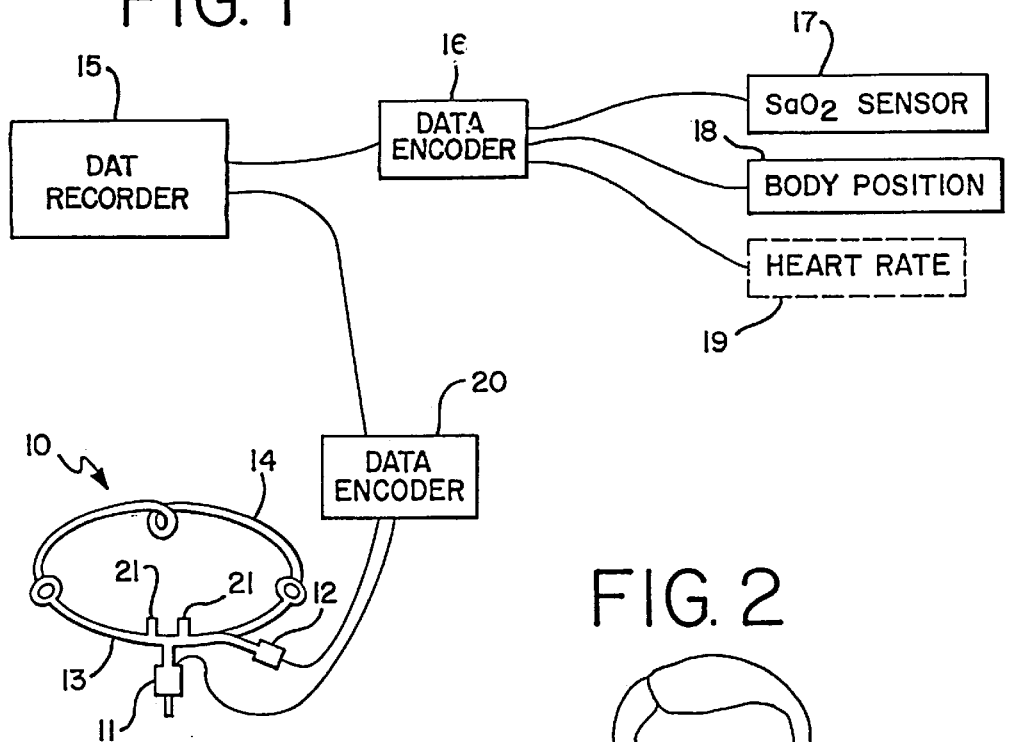
FIG. 1 is a block diagram illustrating a specific embodiment of a data recording apparatus in accordance with the invention.

The incorporated Microfiche Appendix includes a Table 1, Appendix 1, Appendix 2 and Appendix 3. Appendix 1 lists the source code routines of the present invention. Table 1 provides key routines corresponding to the processes depicted in FIGS. 5 and 6. Appendix 2 contains a list of the text within FIGS. 5 and 6 along with references. Appendix 3 is a source code listing of a method of classifying respiratory sounds under an embodiment of the invention.

BRIEF DESCRIPTION OF THE PREFERRED EMBODIMENT

The solution to the problem of analyzing sleep disorders lies, conceptually, in data logging appropriate physiological characteristics (such as sound, body position, blood oxygen levels, et cetera) of a sleeping subject and using the logged data within a formalistic process to identify types and sources of sleep disorders. It has been determined that frequency content of snoring of most subjects will differ based upon the structural source within the upper airway causing the snoring. The frequency of snoring caused by the palate and uvula will differ, for example, from the frequency content of snoring caused by sites lower in the throat. Further determination that a sleeping subject snores through the subject's nose instead of the subject's mouth (or visa versa) may be used to eliminate certain structures as possible sources of the snoring.

The technique of analyzing sleep disorders provided under the invention localizes the source of the sleep disorder based upon information contained within the logged data. Under the invention, apnea and hypopnea are identified by comparison of characteristic parameters within the logged data with characteristic threshold values. Snoring, on the other hand, is analyzed by relating the frequency content of the snoring with upper airway structural sources. To identify structural sources, an analysis is performed within the frequency domain on an audio portion of the logged data to identify and measure fundamental frequencies and harmonics associated with the upper airway structures of the subject's breathing passages. It has been determined empirically that snoring sounds associated with structures such as the soft palate and uvula have fundamental frequencies that are typically in the range of from 20–300 Hertz while snoring originating from other structures (other than the throat) lie at higher frequencies. Throat snoring, while having frequencies in the range of from 20–300 Hz has a diffuse frequency content.

It has also been determined that snoring sounds emanating from nasal passages have higher fundamental frequencies than sounds originating from the mouth. Snoring sounds originating from the mouth, while lower in fundamental frequencies, are also somewhat more diffuse in frequency content.

The tonsils of some subjects have been determined to affect the fundamental frequency of snoring. Where the tonsils interfere with movement of the tongue and uvula, a fundamental frequency of greater than 130 Hz would be expected.

FIG. 4 is a flow chart describing the method used under an embodiment of the invention. Reference will be made to FIG. 4 as appropriate to provide an understanding of the invention. It is to be understood that under the invention some steps of the invention may be performed manually or the entire process of FIG. 4 may be executed automatically under the control of a general purpose computer.

To facilitate analysis of respiratory and snoring sounds, the data logged audio information is limited to a frequency range of from 0–1250 Hertz. Local maxima are then identified within the audio information as well as gaps in respiratory sounds exceeding 10 seconds. Where gaps in excess of 10 seconds are detected, an output is provided indicating possible apnea.

A frequency domain conversion [i.e., a fast Fourier transform ("FFT")] is performed on the audio information. The fast Fourier transformed audio information is then examined at the temporal locations of the previously identified local maxima. Where the results of the FFT at the sites of the local maxima indicate that the local maxima is predominantly made up of a fundamental frequency in the proper frequency range and multiples of the fundamental, a determination is made that the sleep disorder is a soft palate event associated with the palate and uvula (velum snore). Identification of the sleep disorder to be a soft palate event provides the beneficial effect of indicating, in advance of surgery, that UPPP will, more likely than not, be successful.

Data logging under the invention may be accomplished by any of a number of prior art methods. Heart rate, respiratory and snoring sounds, oxygen saturation of the blood and body position information, for instance, may be recorded as in U.S. Pat. No. 5,275,159, the disclosure of which is hereby incorporated by reference. Respiratory exertion may also be recorded from a strain gauge encircling the chest or abdomen of a sleeping subject. Under a preferred embodiment of the invention, a digital audio tape (DAT) recorder, Walkman AVLS, model TCD-D7 made by the Sony Corporation is used for logging audible and physiological events.

Turning now to FIG. 1, a two-channel DAT recorder 15 is shown in conjunction with a number of sensing devices 10, 17, 18 and 19. The $SaO_2$ sensor 17 is a conventional blood oxygen sensor that may be used to determine blood oxygen saturation based upon spectral absorption of a beam of light passing through a body appendage such as a finger or an earlobe. The body position sensor 18 may be a plastic tetrahedron with a metal ball inside and wires located at each apex of the tetrahedron and wherein body position is determined by the metal ball making contact with the wires at a particular apex of the tetrahedron. The optional heart rate detector 19 may be an acoustic detector. Other suitable alternative sensors for oxygen, position and heart rate are known in the art.

Figure 2:
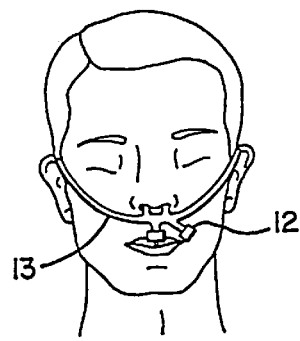
FIG. 2 is a perspective view of a specific embodiment of an acoustic pick-up device on the head of a subject in accordance with the invention.

The sensor 10 in one embodiment is an acoustical pick-up device for respiration and snoring sounds originating from the nose or mouth of a sleeping subject. The mode of use of this sensor 10 may be more fully appreciated by reference to FIG. 2 where a strap 14 (not shown in FIG. 2) of the sensor 10 is placed around the head of the subject, thereby holding an acoustic pick-up tube 13 in proximate relation to the nose and mouth of the subject. Two short tubes 21 positioned at the nostrils of the subject (FIG. 2) conduct sounds from the nose of the sleeping subject through the pick-up tube 13 to a microphone 12. An optional second microphone 11 may detect respiratory and snoring sounds from the mouth of the subject. Alternatively, mouth and nasal sounds may be detected by microphone 12 by using a short tube in place of the microphone 11 to conduct sound from the mouth to the pick-up tube 13.

Optionally, a single microphone may be placed approximately 40 centimeters from the nose and mouth of a sleeping subject (or a single contact microphone may be placed on the throat of the sleeping subject) for the acoustical pick-up of respiratory and snoring sounds. The use of the sensor 10 or optional microphones has been determined to be more effective in detecting the sounds of snoring and/or airflow because of the proximity of the sound source to the sensor 10. Such detectors have been found useful under the invention in collecting apnea information as well as in providing improved signal-to-noise ratios.

Data encoders 16 and 20 are used to encode data for recording on each of the two channels of the DAT recorder 15. Data encoder 20 frequency limits microphones 11 and 12 to a bandwidth from 20–1250 Hertz and (where signals from two microphones are to be recorded on a single channel) may frequency shift (e.g., by modulating onto a 5 Khz carrier) the output of one of microphones 11 or 12 to a non-conflicting location within the 0–20 kilo-Hertz bandwidth DAT channel such that audio information from microphones 11 and 12 may be recorded and, later, separately recovered without loss of information. Other suitable encoding schemes are well known in the art.

Data encoder 16 may function similarly to data encoder 20 to encode data from the sensors 17, 18, 19, or use some other, simpler encoding process. Since the output of sensors 17–19 is analog and very low frequency, the information from the three sensors 17–19 may be either frequency shifted for storage on the DAT channel, as with encoder 20, encoded under a time division multiplex (TDM) format, or otherwise encoded to permit multiple sensor outputs to be recorded on a single channel. Alternatively, separate recording channels can be used to record each sensor output.

To maximize recording efficiency, the data encoder 20 may buffer 2–3 seconds of data and may compare a sound level at an input to the buffer with a number of threshold levels, including a first and second sound amplitude threshold values. (The first threshold may be referred to as an apnea threshold and the second threshold referred to as a snoring threshold). When the sound level rises above the first threshold, recording may be discontinued after some time period (e.g., 30 seconds). When the sound level falls below the first threshold (indicating breathing has stopped) recording may be restarted, resulting in 2–3 seconds of buffered data (occurring before the threshold transition) being recorded first. If the sound level stays below the first amplitude threshold for a third time period (e.g., 90 seconds) (indicating that the subject has awakened or the microphone has fallen off) the recorder may be again stopped.

Where the sound level exceeds the snoring threshold, recording is started after a fourth time period (e.g., 1 second) with, again, the buffered data recorded first. When the sound level falls below the snoring threshold, the recorder continues for a period allowing the sleeping subject to draw another breath. If the sound level does not again exceed the snoring threshold for a fifth time period (e.g., 45 seconds) recording may be again stopped.

Figure 3:
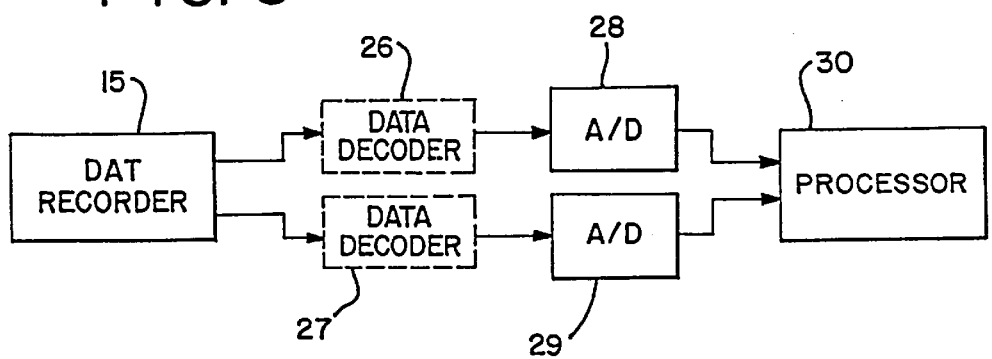
FIG. 3 is a block diagram of a specific embodiment of an apparatus for analyzing data from a subject in accordance with the invention.

After recording of physiological events for an appropriate period of sleep (e.g., 4–8 hours), the DAT recorder 15 is disconnected from the sleep subject and the results analyzed. To facilitate recovery of the recorded data, the DAT recorder 15 is interconnected (FIG. 3) with a general purpose computer (processor 30) through analog to digital converters (A/D's) 28, 29. Decoding (and separation) of individual microphone 11, 12 outputs may be accomplished digitally within the processor 30, as is well known in the art, or within optional decoders 26 or 27. Likewise, recovery of sensor 17–19 outputs may be accomplished within the processor 30 or within the decoder 26 or 27.

Under one embodiment of the invention, recovery of data occurs at a very rapid rate by replaying the recorded data at 2–4 times recording speed into A/D's 28, 29 with frequency downconversion occurring within the processor 30. Alternatively, a number of A/D's are provided and data from many recorders 15 are recovered in parallel by the processor 30 with the data from each recorder placed in a separate file for later analysis.

Upon transfer of the raw data into the processor 30, a first file containing audio information is created by the processor 30. The file is used by the processor to monitor the sound of the sleeping subject and identify breathing and snoring events. To facilitate data analysis, the processor 30 creates a sound envelope of breathing activity detected by each audio sensor.

To create a sound envelope, the processor 30 breaks the raw data into overlapping blocks (e.g., 300 samples per block with 100 samples at a first end overlapping a previous block and 100 samples at a second end overlapping a subsequent block). An absolute value of the largest sample of each block is stored in a reduced data file along with information detailing the location within the raw data of the largest sample of each data block.

Since the reduced data file contains a summary of the largest samples over a number of data blocks, the contents of the reduced data file may be displayed on a computer terminal as a sound envelope representation of the raw data file. Also, because of a 200:1 data reduction, several minutes of raw data may be displayed on the terminal as a sound envelope that is representative of the contents of the raw data file.

Under an embodiment of the invention drawn primarily to practicing the invention under a manual mode, an operator (not shown) of the processor 30 may use the sound envelope to identify likely episodes of apnea, hypopnea, or snoring. Using appropriate icons, the operator may scroll the sound envelope or raw data displayed on the terminal forward or backward to quickly identify profiles within the sound envelope or raw data indicating such events. An icon such as a time bar may be used in conjunction with scroll icons to quickly move from one area of recorded data to another. Split screen capability is also provided such that sections of this sound envelope (or raw data) may be compared with other sections of data. The operator may identify such episodes to the processor 30 by clicking and dragging a computer mouse across such an episode displayed on the monitor. Upon identifying an episode in such a manner, the processor 30 retrieves corresponding raw data and reconstructs the sound of the raw data through an audio speaker proximate the operator. Using such a method, an operator may differentiate between episodes of no breathing or inefficient breathing (apnea or hypopnea) and episodes of very quiet breathing. The operator may also use such an approach to differentiate between snoring and coughing or sneezing.

Alternatively, an operator may be trained to monitor the raw data through an audio speaker with the raw data played at 2–4 times the recorded speed. Upon identifying suspicious intervals, the operator may return the speed of play to a normal rate to hear a normal reproduction of a suspicious event.

In the case of apnea or hypopnea, the operator may identify such episodes by listening 100 to the sound and noting a duration of such an episode. Where episodes exceed some predetermined time length (e.g., 10 seconds) 102, the operator may cause that part of the sound envelope to be surrounded by a box (marker) and labeled with an appropriate character (e.g., "A" for apnea or "H" for hypopnea). The processor tabulates a total number of labeled boxes for the later generation of a summary.

In the case of snoring, the operator selects a section of data with an indication of snoring 103 and causes the processor 30 to do a frequency domain conversion (e.g., a fast fourier transfer) 104 on the selected data. [Fast fourier transformation may be accomplished by using the program provided on page 163 of *The Fast Fourier Transform* by E. Oran Brigham (Prentice-Hall 1974)]. The processor 30, upon transforming the data then displays the results for the benefit of the operator.

Fast fourier transformation (FFT) allows an operator to examine the frequency components of selected snoring events. Since different sections of the upper airway generate different signatures (frequency components), the identification 105 of those frequency components in the selected data provides a means of diagnosing the source of the snore. The most significant contributors to snoring in the upper airway (and the best candidate for UPPP) is the uvula and soft palate.

Snoring generated by the soft palate has a distinct pattern. A fundamental frequency of snoring generated by the soft palate is typically between 25–150 Hz and depends on the size of the uvula and soft palate, whether the snoring takes place during the inhalation or exhalation and whether the snoring was nasal or oral, or both. To evaluate fundamental and harmonic information within an episode (epoch), the operator characterizes the FFT data using a snore index 106 (e.g., where the episode is primarily of a fundamental and harmonics, a snore score of 1 is assigned and where fundamental or harmonics are negligible, a snore score of 5 is assigned). A snore index can be calculated as an average of the snore scores. The processor 30 tabulates the snore index and location as each episode is evaluated for purposes of the later generation of a summary report.

The fundamental frequency of snoring often changes during a snoring epoch (e.g., during inhalation or exhalation) because of changes in the size of the airway, air flow rate, etc. As a consequence, harmonics of the fundamental frequency are also present and changing. To accommodate and identify fundamental frequencies in a changing physical environment, the operator may be forced to reduce the affect of frequency changes in the search window. Narrowing the search window will often allow an episode that may originally have been a snore score 5 to be rated at a much lower snore score number. Narrowing the search window (reducing a terminal size of analogical data) offers such benefits by examining a much shorter term period where any shift in the fundamental frequency would presumably be much smaller. On the other hand, a narrow search window is to be avoided wherever possible because the use of a broad search window provides better resolution which is important at low frequencies.

It has been determined that an excellent candidate for UPPP is a subject with an identifiable fundamental and harmonics in each snoring epoch and very little energy in other frequencies (snore score=1). If the fundamental and harmonics are not easily identifiable, then the soft palate and untribution to the snoring or that there may be other important sources of the snoring. (UPPP in such a case would be less successful in reducing snoring).

To simulate the effects of UPPP, the operator may eliminate 107 the fundamental frequency and harmonics within an episode, and simulate the effect through an audio speaker. The operator may eliminate the fundamental frequency and harmonics by individually selecting each frequency on the display of the processor 30 and activating a delete or attenuation function. Simulation of the effect is accomplished by performing an inverse fast fourier transform (IFFT) and routing the result to an audio speaker. A simulation of the effect of UPPP may then be determined by comparing decibel levels 108 of the original snores played back and the snores after deletion/reduction of fundamental/harmonics. Where differences in decibel level exceed some threshold value 109 (e.g., 17 db) a snore score of 1 would be indicated. A snore index of 1 is an indication of a soft palate event 111. Where the difference is some other threshold (e.g., less than 17 db), a higher snore index may be assigned indicating snoring of mixed origin 111.

Upon completion of analysis under the manual mode, a summary report may be generated by the processor 30. The summary report may include tabulations of such events as total number of apnea/hypopnea and snoring events detected within the data. Based upon the number of snore events a listing may be provided as to the number of snore events assigned to each snore index. Based on the distribution of snores among the snore index values a projection as to the site of snoring generation may be provided as part of this summary.

In another embodiment of this invention, sleep analysis (snoring, apnea, etc.), and report generation may be performed automatically by the processor 30. To analyze sleep disorders, the processor 30 identifies breathing events and searches for temporal gaps in such breathing events for apnea and hypopnea. The temporal gap between may be analyzed for apnea and hypopnea. Also, when the period between inhalation and exhalation (or intervening non-breathing event) have been identified, the analysis of snoring may be limited to more relevant areas.

Figure 5A:
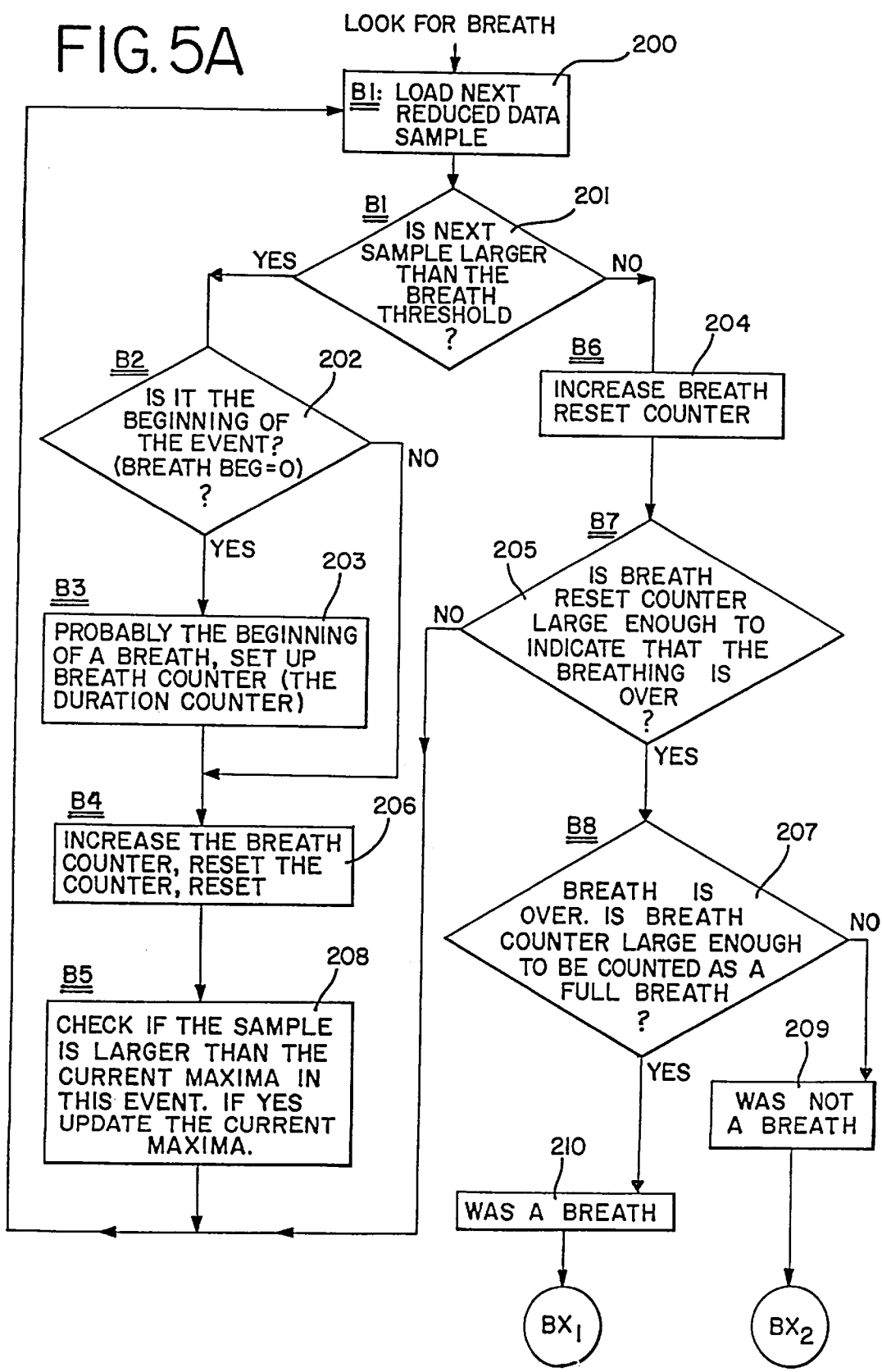
Figure 6A:
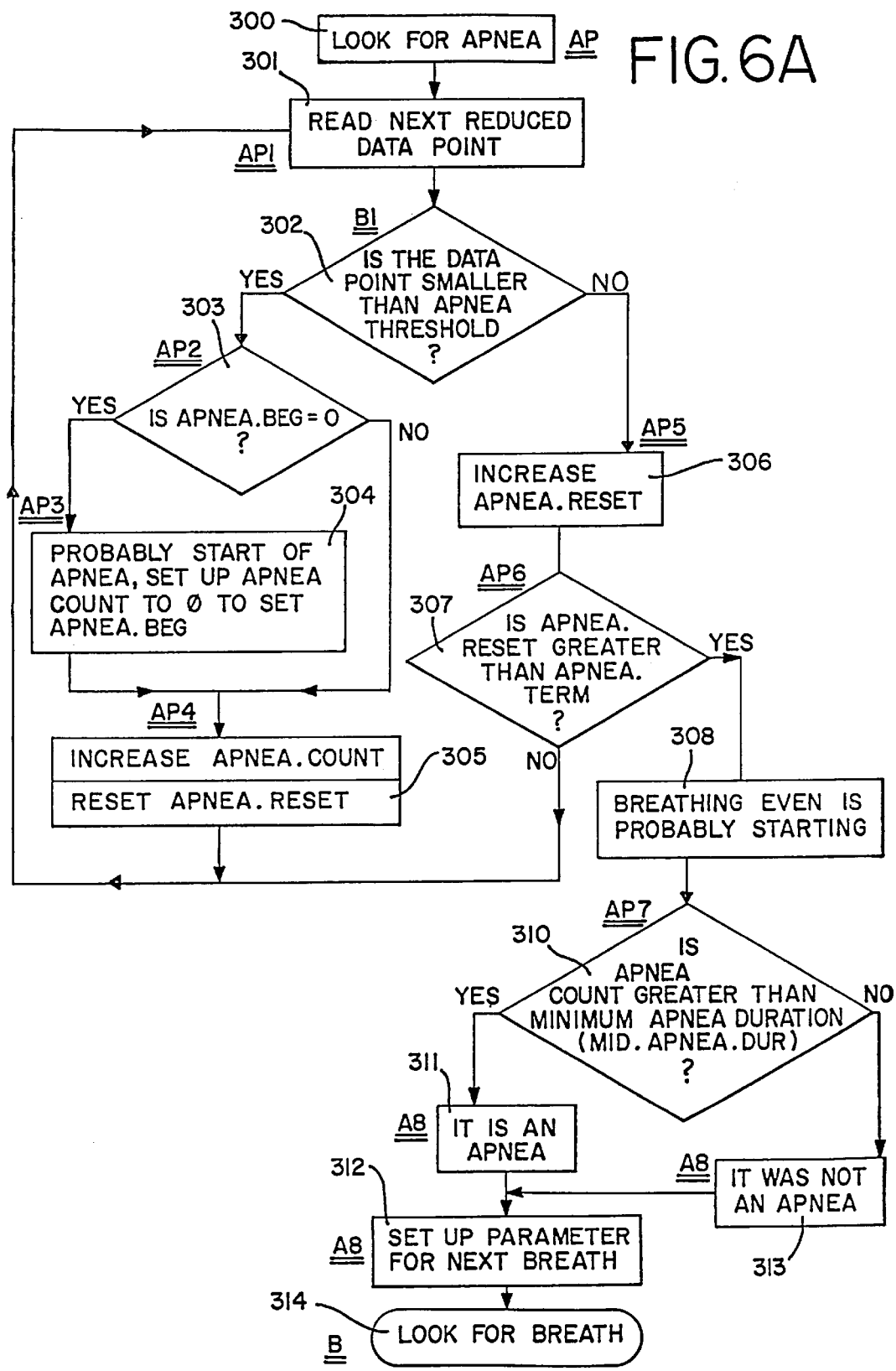
Figure 6C:
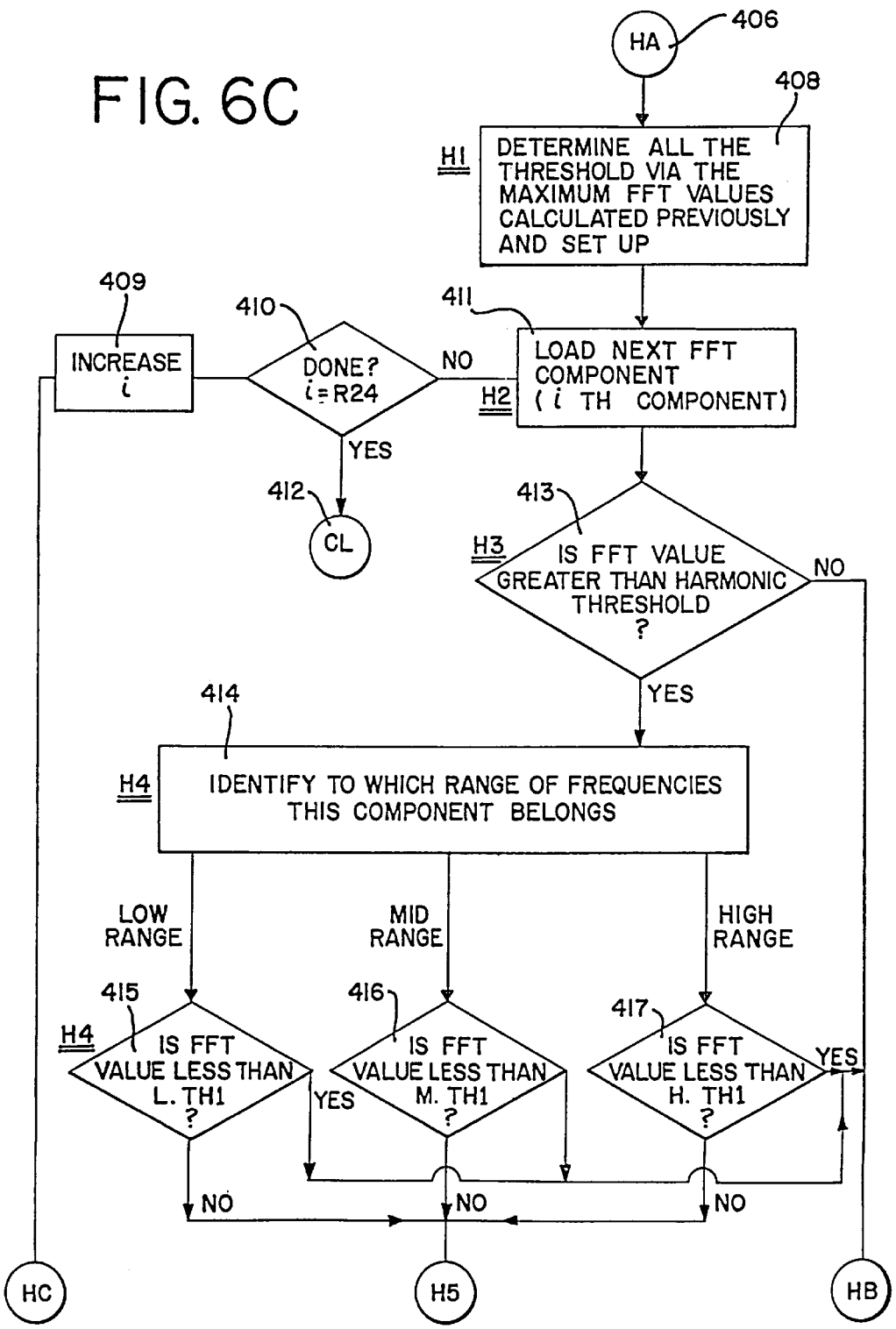
Figure 6D:
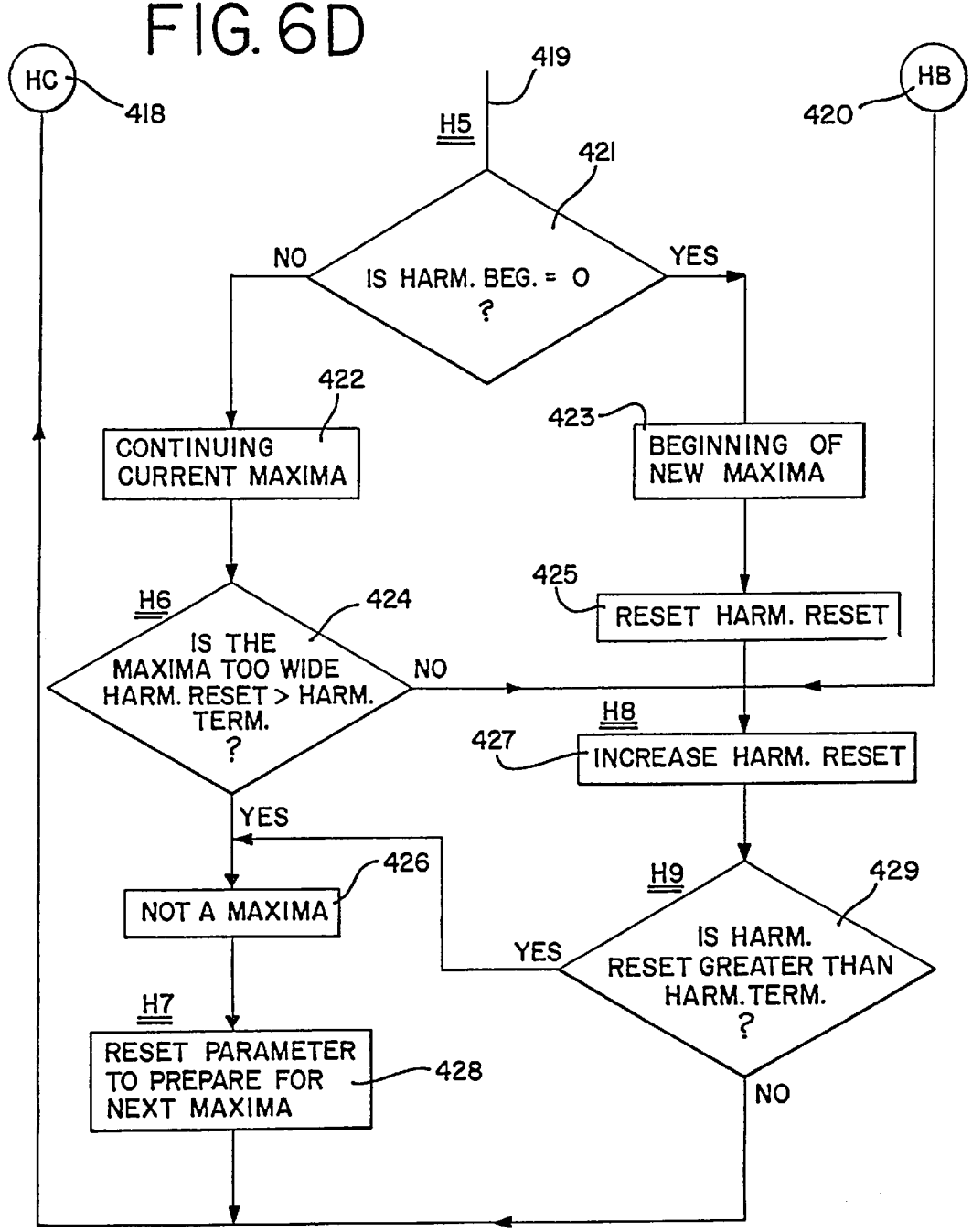
Figure 6E:
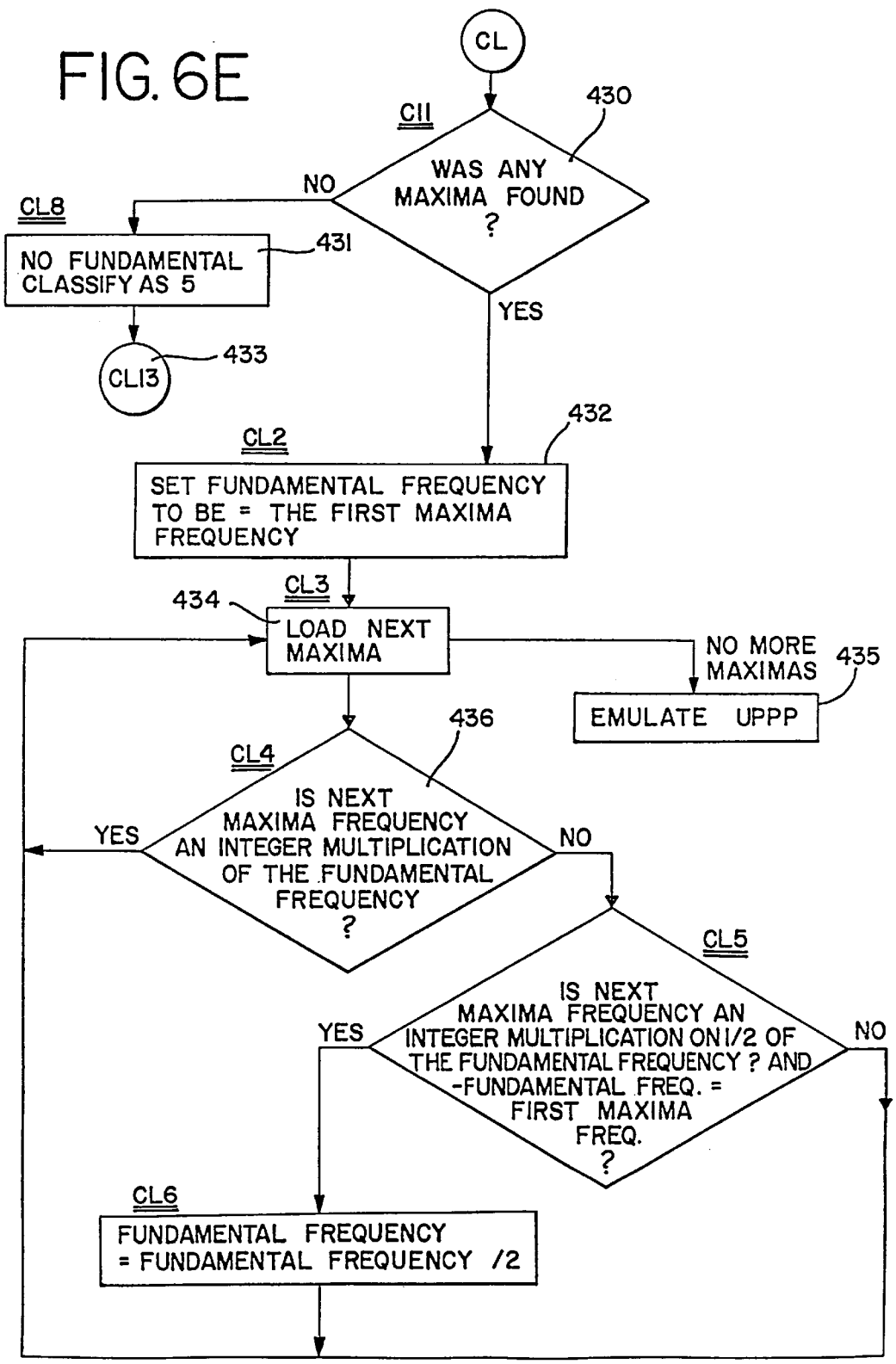
Figure 6F:
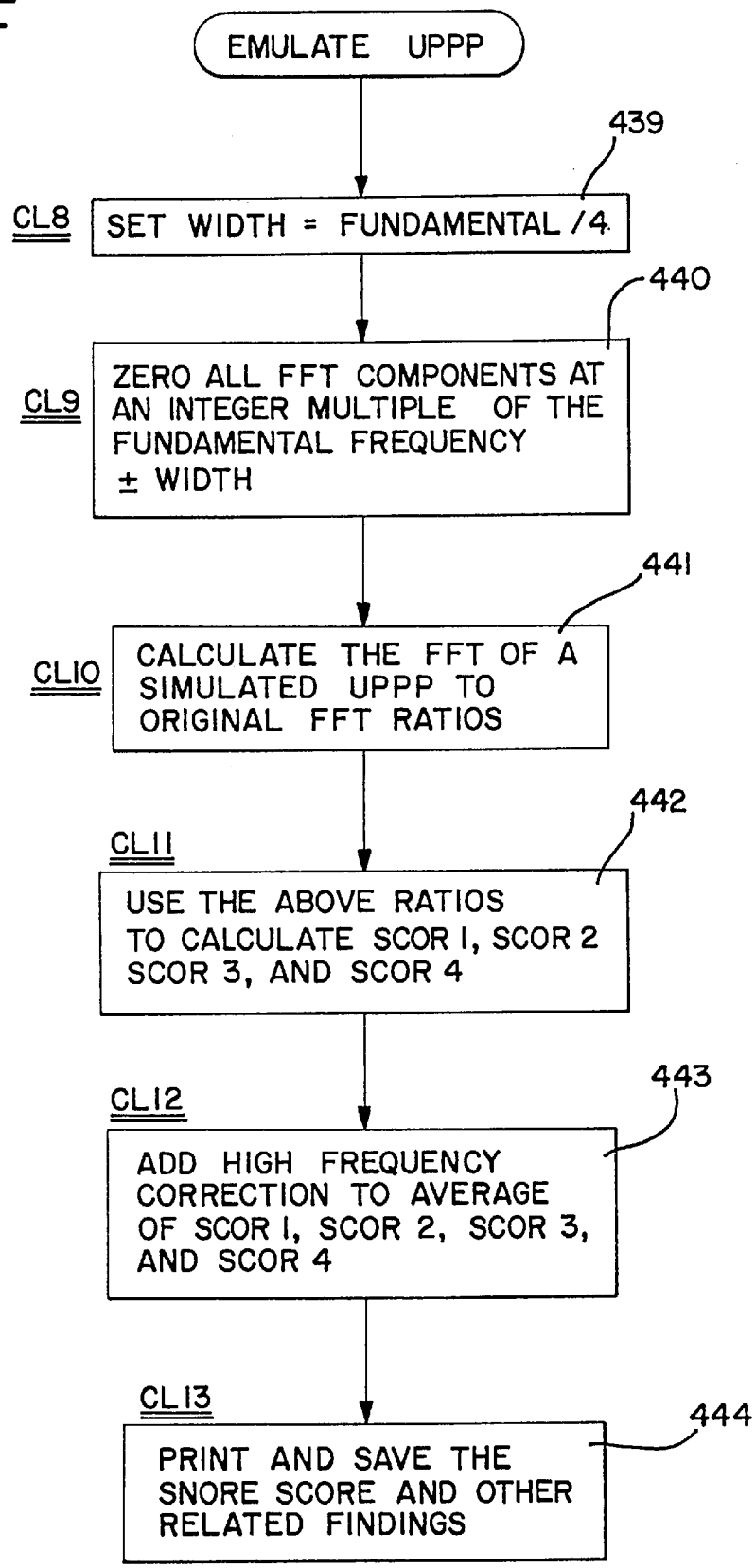

Turning now to the identification of breathing events, a block diagram of the process may be found in FIG. 5. Reference will be made as appropriate in the explanation of blocks of FIG. 5 to corresponding locations source code in Appendix 1 (see Microfiche Appendix). References to Appendix 1 (see Microfiche Appendix) will be to alphanumeric characters (B1–B8) located in the left margins.

In the identification of breathing events, the data source is the reduced data file. After each sample is retrieved 200 from the reduced data file, the sample is compared 201 (source code location B1) to a breathing threshold level (breath.thresh). If the data sample exceeds breath.thresh, then a determination is made 202 of whether the data sample is the first of a breathing event (breath.beg=0) (source code location B2). If the sample is the first of a breathing event, then a breath counter is set to zero 203 (source code location B3). To measure the duration of the breath. After the breath counter is set to zero 203, or if the sample wasn't the first in a breathing event, then the breath counter is incremented 206 (source code location B4). A breath reset counter is also reset. A comparison is then made as to whether the current sample is the largest sample for that breathing event 208 (source code location B5). If the current sample is the largest sample, then a previous maximum is replaced by the current sample.

Through the blocks described 200–208, the breathing event detector (FIG. 5) measures the duration of the breathing event and locates a relative maximum for that breathing event. At the end of the breathing event (or during apnea) data samples no longer exceed the breath threshold and a different path is taken out of block 201.

After a breath is over (breath samples no longer exceed breath.thresh), the samples are each used to increment 204 (source code location B6) a breath reset counter. The contents of the breath reset counter are then compared with a threshold 205 (source code location B7) to determine if enough continuous samples below the breath threshold have been received to indicate that the breathing event is over. If so, the contents of the breath counter are then compared with a threshold 207 (source code location B8) to determine if the number of continuous samples exceeding the threshold were enough to consider the breathing event a full breath.

After the termination of breathing events, the breath threshold, an apnea threshold, and a hypopnea threshold are recalculated 211 (source code location B10) based upon an average 210 (source code location B9) of the last 10 breath maxima. Afterwards, or if the breathing event were determined to be a breath, then an apnea counter (apnea.count) is set equal to a current value of non-breath samples (breath.reset) and the processor 30 proceeds to look for apnea.

To this end and in a general sense, the processor 30 identifies gaps 100 with very little or no respiratory sound. Gaps are identified by comparing sound levels within a moving ten-second block of audio information with a threshold value. Where the sound threshold (apnea threshold) is not exceeded for ten continuous seconds 102 (and did not continue for more than 90 seconds), the processor 30 outputs indication 101 that the subject may have sleep apnea. In addition, the processor 30 may output an indication of blood oxygen level during the gap along with sleep position or may defer providing indication of sleep apnea unless the blood oxygen level falls below a threshold level.

During each breathing event (FIG. 5) whenever the breathing threshold (breath.thresh) is not exceeded for a number of samples exceeding a breath-reset threshold 205, the processor looks for apnea (FIG. 6). The processor 30 looks 300 for apnea by reading another data sample 301 (source code location AP1) and compares the data sample with an apnea threshold (apnea.thresh) 302 (source code location B1).

If the data sample does not exceed the apnea threshold, then a determination is made as to whether the sample is the beginning of an apnea interval 303 (source code location AP2). If the sample is the beginning of an apnea interval, an apnea counter (apnea.count) is set to zero 304 (source code AP3). Afterwards, or if the sample was not the beginning of an apnea event, an apnea counter (apnea.count) is incremented 305 (source code AP4) and an apnea reset counter (apnea.reset) is reset. For as long as the apnea period continues, the processor 30 processes data samples through blocks 301–305, each time incrementing the counter apnea.count.

At the end of an apnea period (the data sample exceeds apnea.thresh), the apnea reset counter is incremented 306 (source code AP5). When enough continuous samples exceeding the apnea threshold have been processed, such that the incrementing apnea reset value 306 exceeds a threshold 307 (source code AP6) a determination is made 308 that breathing has again begun.

After breathing again starts, a determination is made as to whether the duration of the apnea interval exceeded a threshold value 310 (source code AP7). If they were, the interval is an apnea event 311 (source code A8). If not, the interval was not apnea 313 (source code A8) and sets breathing parameters 312 (source code A8) to examine another breathing event.

Following the analysis of apnea, the processor 30 then analyzes snoring events. In a general sense and to be able to analyze snoring, the processor must be able to identify local maxima within the raw data.

To identify 103 local maxima, the processor examines a moving one-half second block of audio information for the highest relative magnitude audio event. To ensure that the maxima is a significant event, the processor compares the maxima with adjacent audio information within the one-half second block to ensure that the maxima is at least twice the average of the magnitude of adjacent information within the one-half second block. In processing the raw data, the processor 30 creates a second file detailing the location of the local maxima within the raw data.

The raw data containing the local maxima is then fast fourier transformed 104 and may be stored in a third file by the processor 30. The previously identified local maxima are examined. Where the fast fourier transformed local maxima are comprised primarily of a fundamental frequency between 20–300 Hertz, and harmonics of the fundamental frequency, the processor 30 outputs 111 an indication that the snore or sound is substantially a soft palate event.

To facilitate the FFT in the illustrated embodiment, 1,024 data points (i.e., samples) centered around the local maxima are selected for transformation. Following transformation, a fundamental frequency is identified by finding a second set of maxima within the FFT data. Maxima within the FFT data are identified by calculating a smoothed FFT for each FFT data point. The smoothed FFT ($S_i$) is calculated as follows:

$$S_i = \frac{1}{2m_i + 1} \sum_{i-m_i}^{i+m_i} F_i$$

where "i" is the frequency, $F_i$ is the FFT amplitude at the "ith" frequency, $M_i$ is the smoothing order (e.g., 4), and 20 Hz<i<300 Hz. To determine a maxima each $S_i$ is compared with its neighbors on each side. $S_i$ is a maxima if $S_i$ is greater than or equal to $S_j$ for all $i-m_2<j<i+m_2$ where $m_2$ is a range of evaluated FFT data points (e.g., 10). An actual maxima is determined around each frequency of $S_j$ ($i_{sj}$) for one data point is less than or equal to $S_j$ is less then or equal to $m_2$ data points. An FFT point is a maxima ($F_{imax}$) if $F_{imax}$ is greater than or equal to $F_{ik}$ for any $i_k$ where $i_{sj}-m_2<i_k<i_{sj}+m_2$.

Insignificant FFT maxima are eliminated by considering surrounding FFT data points. If the magnitude of surrounding FFT points do not drop to some proportional value (e.g., ⅓) within $M_3$ FFT points (e.g., 10) and stay below the proportional value for an additional $M_4$ FFT points (e.g., 40), then the FFT maxima is dropped from consideration. To state the premise in another manner $F_{imax}$ is a significant maxima if $F_{imax}$ is >$3F_i$; where $i_{max}-M_3-M_4<i<i_{max}-M_3$.

Once the insignificant FFT maxima have been eliminated, the remaining FFT maxima are ordered in terms of increasing frequency. An attempt is made to group FFT maxima in terms of a fundamental frequency and its harmonics. The first FFT maxima of the ordered group, at the lowest fundamental frequency $i_1$, is used to identify harmonics through the use of the equality $i_k=i_1*1\pm\delta$ where $i_k$ is a harmonic of $i_1$, 1 is an integer greater than one, and $\delta$ is an allowed error (e.g., 1). Any FFT maxima at a frequency of $i_1$ and $i_k$ is considered part of a harmonic group which included the fundamental frequency and any harmonics.

The process can be repeated for the next fundamental frequency (FFT maxima) of the remaining FFT maxima within the ordered group. The FFT maxima at the next highest frequency i2 (and multiples) become part of a second harmonic group. The process may be repeated again and again until more FFT maxima have all been included in some harmonic group.

It has been noted in some cases that a fundamental frequency may not be included within the original group of FFT maxima. When this happens, it will not be possible to group some FFT maxima of the ordered group of FFT maxima within a harmonic group. One means of solving this problem is to divide the frequency of the lowest frequency FFT maxima of the remaining ordered group by 2 (or 3) and use the result as a fundamental frequency. Using such a procedure can make it possible to place more FFT maxima within a harmonic group.

Once the FFT maxima have been placed into harmonic groups, the harmonic groups having fundamental frequencies in the range of from 20–300 Hz are identified 105. Since it has been determined that snoring having fundamental frequencies in the range of from 20–300 Hz is an event primarily associated with the structures of the soft palate and uvula and since UPPP can be effective in reducing snoring produced by the uvula, the determination of the contribution of sound produced by the uvula provides an important benefit.

To evaluate the sound contribution of the soft palate and uvula, the identified 105 harmonic groups having fundamental frequencies in the range of from 20–300 Hz are subtracted 107 from the original sounds of snoring and the decibel reduction in volume of the FFT residual maxima evaluated 108. If it is noted that the reduction exceeds some threshold (e.g., 17 db) 109, then the site of snoring generation is the velum and the subject may be a good candidate for UPPP 111.

To facilitate a comparison of sound levels, the FFT maxima (data points) of the identified harmonic group are subtracted from the original fast fourier transformed data and the result is optionally stored in a fourth file. To obtain a decibel comparison between the FFT points in the third and fourth files, a weighing factor must be associated with each of the FFT values within each data file based upon frequency. Through the use of the weighing, the loudness of the third and fourth files can be compared. Given an FFT value of $F_i$ (0<i<N−1 and N is the order of the FFT volume), the effective loudness L(f) in Db can be determined by evaluation of the function as follows:

$$L(f) = 10 \log_{10} \sum_{i=0}^{N-1} W_i F_i$$

If the loudness of the original data is greater than 50 phons, then relative weight values for a range of frequencies can be described as follows:

W1000 Hz=W100 Hz×(3.2)

W500 Hz=W100 Hz×(2.5)

W200 Hz=W100 Hz×(1.8)

W100 Hz=W 50 Hz×(1.8)

To determine an absolute set of weight values, an arbitrary weight value may be chosen for a particular frequency (e.g., W 100 Hz=1) and weight values determined for other frequencies either directly from the above equations or by extrapolation.

Alternatively, linear weight values may be used. Other weighting schemes (e.g., logarithmic, et cetera) may also be used in accordance with the invention.

In one embodiment of this invention, the above process is more fully described in FIG. 6. Following FFT 400, a density function is calculated for low frequency components of the FFT of from 20–350 HZ. The density function is calculated 401 (source code R1) in accordance with the invention by integrating the FFT across the frequency range (20–350 HZ) and dividing by the number of frequency components integrated. Likewise, a density function is calculated for mid-frequencies (350–750 HZ) 402 (source code R2) and for high frequencies (750–1200 HZ) 403 (source code R3).

The density functions are then compared 404 (source code R4). If the low frequency density function is greater than the mid-frequency, and/or the mid-frequency is greater than the high-frequency density, then the event is determined to be snoring 405. If not, then the event is not a snore 407. (Corresponding references HA and 406. HC and 418, H5 and 419, HB and 420, CL13 and 433, and EMULATE UPPP and 435 indicate connection only). Another way to detect whether a breathing event is a snore, is to use another microphone not in the air flow path and to use a simple amplitude threshold criteria to identify snoring.

Following a determination that an event is snoring, a set of threshold values are calculated 408 (source code H1). An FFT sample is then loaded 411 (source code H2) and compared with a threshold value 413 (source code H3) to ensure that the FFT sample is not outside a range of interest.

If the FFT sample is within the range of interest, then a determination 414 (source code H4) is made as to where it falls within the spectrum (low, medium, or high) and the FFT sample is then compared 415–417 with an appropriate threshold value L.TH1, MTH1, or H.TH1) to eliminate insignificant peaks.

If the FFT sample is greater than the relevant threshold, then a determination is made 421 as to whether the sample is the first FFT sample of a new maxima 423. If it is the first FFT sample of a new maxima, then the counter harm.reset is reset.

If the FFT sample is not the first FFT sample of a maxima, then a current harm.reset value is compared with a threshold value 424 (source code H6) and incremented 427 (source code H8) before being compared a second time with the threshold value 429 (source code H9). If in either comparison 426, 429 it is determined that the value of harm.reset exceeds the threshold (harm.term) the FFT sample is outside the range to be considered and is not a maxima 427 and the parameters are reset 428 (source code H7) for consideration of another maxima. If harm.reset value of an FFT sample were less than the value of harm.term, then the FFT sample will be retrieved under pre-existing parameters.

A sample number, "i", is incremented 409 and the incremented sample number compared 410 to an event size (1024 samples). If the sample number is less than the event size, then another sample from the same maxima is retrieved 411. If not, the processor 30 proceeds 412 to look for fundamentals and harmonics.

The processor first tests if one of the identified frequencies was a maxima 430 (source code C11) indicating the presence of a fundamental frequency. If no fundamental is found, the event is rated 431 (source code CL8) as a snore index 5 and the result reported 444 (source code CL13) to a summary file.

If a maxima is found 430 the processor 30 determines the fundamental frequency to be the first maxima frequency 432 (source code CL2). The processor 30 then loads a next maxima 434 (source code CL3) and determines 436 (source code CL4) if it is an integer multiple of the fundamental. If so, another maxima is loaded 434 and considered 436. If not, the processor attempts to determine 437, 438 whether the first maxima is a multiple of the fundamental.

Follow the identification (grouping) of fundamentals and harmonics 106, the processor emulates the effect of a UPPP. The processor first sets 439 (source code CL8) a frequency width equal to the fundamental frequency divided by 4. The processor then zeros 440 (source code CL9) all FFT harmonic values closer than the calculated frequency width to the fundamental and the harmonics frequency. An FFT is then calculated 441 (source code CL10) of a simulated UPPP to the original FFT ratios. The ratios are then used to determine 442 (source code CL11) a source index which is then corrected 443 (source code CL12) before saving and printing 444 (source code CL13) a summary report. A normalized snore index for each snore index classification (1–5) may be calculated by squaring the snore index for each event of each class, summing the squared indexes of each class, and dividing the summed indexes of each class by the summed total of all classes.

The summary may include a list of the dominant fundamental frequencies as well as secondary fundamentals detected. An estimation of the relative energy in the fundamental (and harmonics) as opposed to all frequencies, may be provided. The energy content of certain fundamental frequencies, compared to appropriate threshold values, may be used as an indicia of snoring from multiple sources or, otherwise, as an indicia of a velum snore. The relative energy content of fundamentals and harmonics of from 20–300 Hz and harmonics against total energy of sound may be calculated and included in the summary as a velum snore index.

The summary may identify the soft palate of the subject as the source of the snoring and label the snoring as a velum snore when the sound is predominantly of a fundamental frequency of from 20–150 Hz and harmonics, and a non-velum snore involving the tonsils when the fundamental frequency is above 130 Hz. Where the FFT indicates a diffuse sound, the summary may indicate a non-velum snore implicating the pharyngeal and nose or otherwise a mixed source when the snoring contains an indicia of multiple sources, such as when the energy of fundamental frequencies and harmonics compared to total sound is below a threshold. The summary may also provide an indication of the different types of events occurring during a sleep interval by indicating a velum snore index from the total velum, non-velum, and mixed snores during a time interval.

In another embodiment of the invention other methods are used to identify the presence of harmonic patterns based in the 20–300 Hz range. One method involves finding a first value "d" and a second value "a" such that during the snoring event the wave amplitude in the time domain will comply with the equation as follows:

$$S(t)=As(t-d)+\delta$$

where "d" is the cycle time of the fundamental frequency in seconds, "a" is an amplitude that is usually close to 1 that changes very slowly, and "δ" is an allowed error. If "d" is greater than 30 milliseconds, then "d" is the fundamental frequency wave length in seconds. If "d" is much less than 30 milliseconds, then "d" will be centered around a harmonic wave length and the equation will be valid for only subsections of the snoring event.

Under an embodiment of the invention, it has been determined that the reliability of recorded snoring data can be enhanced by excluding data generated when a patient awakens momentarily, or for longer periods. The exclusion of data from periods when a patient is awake is important from the point of view that if a patient has been awake during a significant part of a recording period, the breathing patterns of the non-sleeping patient can significantly distort average values associated with sleep and calculated indicia (e.g., apnea or hypopnea indexes).

When a patient is asleep, the breathing pattern is regular and the breaths are deeper. An operator reviewing respiratory data can identify sleep periods by the constant breathing rate where such breathing patterns exceed some threshold time value (e.g, 3 minutes). In addition, wherever a snore is identified a sleep state will be presumed. Further, for purposes of the following analysis, normal respiration will be considered a series of respiratory events during sleep that are not interrupted by coughing, apnea, snoring or speech.

To identify sleep periods, a respiratory rate is calculated for each breathing event. For example, the respiratory rate can be defined as an average time between two successive breaths over the previous 4 breathing events. Under the embodiment, the system will mark a period of time as a non-sleep state if the respiratory rate fluctuates more than a threshold value (e.g., ±10%) for a period of several minutes (e.g., 3 minutes) and/or the breathing amplitude decreases below another fixed threshold value (e.g., 50%).

Under an embodiment of the invention, snore identification may be enhanced by manual evaluation of snoring events. Under the embodiment, a set of respiratory events are randomly selected using known randomization techniques and the results manually analyzed. If the respiratory event selection process is truly random, then the results of the analysis of the random respiratory event set can be applied to the original event set as a whole. For example, if 6 of 10 of the randomly selected events were determined to be snoring events, then it could be safely assumed that about 600 out of every 1,000 events of the general population of samples would also be snoring events.

While the randomly selected event set could be of any size, it is expected that of a total event set of 3500, that at least 300 randomly selected events would be required. Following random selection, the operator classifies the events of the random event set as either snoring or non-snoring by a combination of visual examination of FFT analysis results and/or listening to the breathing events. The operator may also assign a snore index of 1–5, wheeze or artifact.

Under the embodiment of the invention, it has been determined that where a snore is not completely generated by the velum (mixed snore) that the effectiveness of UPPP (or LAUP) may still be determined by calculation of an amplitude distribution index. The amplitude distribution index may be used as an indication of the potential reduction of the loudness of snores during a recording period due to a UPPP (or LAUP) operation.

Under the embodiment, the events determined as snoring are ordered according to descending FFT amplitude. Following ordering, the snores are then grouped, starting with the largest of the ordered group, based upon the previously determined snore index and the percentage of velum snores (snore index of 1 or 2) within the group. It is to be noted that usually the largest amplitude snores of the ordered snores would predominantly be velum snores, whereas at some point the content of the ordered snores would become predisposed toward non-velum snores.

Under the embodiment, grouping of the ordered snores continues until the group contains no more than 85% velum snores. The grouping can then be stopped and the ratio of largest and smallest amplitude snore is determined. The ratio (e.g., log of the amplitude ratio or simply the ratio) (also referred to herein as the amplitude distribution index) provides a reliable indication of the improvement to be expected through UPPP.

Under another embodiment of the invention, snore identification (and determination of the amplitude distribution index) may be enhanced by teaching the computer to identify snoring through use of a snoring template characterized by a number of breath parameters. Under the embodiment, breathing events that have been previously given a snore index of from 1 through 5 may be further classified as snoring/non-snoring events by fitting a set of breathing parameters of the snoring template to a manually analyzed sample set of a relatively small size. Under the embodiment a set of samples (e.g., 150 out of 3,500 recorded events) are randomly chosen using well known randomization techniques. The operator then classifies the events of the 150 respiratory event set as either snoring or non-snoring by a combination of visually examining the FFT analysis and/or listening to the breathing event. The operator also assigns a snore index to each of the randomly selected samples.

Following the manual classification of each of the 150 randomly selected events, a set of 6 values (event parameters) are determined for each breathing event of the 3,500 breathing events. The first value (ldensl) is the average FFT amplitude over the low frequency range (50–300 Hz) of a breathing event. The second value (mdensl) is the average FFT amplitude over the mid frequency range (300–450 Hz) of the breathing event. The third value (hdensl) is the average FFT amplitude over the high frequency range (above 450 Hz). The fourth value (lowmax) is the maximum FFT amplitude in the low frequency range. The fifth value (midmax) is the FFT amplitude peak in the mid frequency range. The sixth value (himax) is the FFT amplitude peak in the high frequency range.

A preliminary set of breathing parameters of the snoring template (template parameters) are then fitted to the 150 manually analyzed events based upon the 6 determined values of each manually classified group of the 150 respiratory events. A first template parameter (Low_High_Dense_Ratio) is determined by dividing ldensl by hdensl for each breathing event of the 150 manually analyzed respiratory events that were determined to be a snoring. The quotients are then averaged and the preliminary value of Low_High_Dense_Ratio is set equal to the averaged value. Likewise, a second template parameter Low_High_Max_Ratio is determined by dividing lowmax by himax for each event of the 150 events determined to be a snore and averaging the quotient. Low_Mid_Dense_Ratio is determined by dividing ldensl by mdensl of each event of the 150 events determined to be snore and averaging. High_Mid_Dense_Ratio is determined by dividing ldensl by mdensl of each snoring event and averaging. Low_Mid_Dense_Ratio is determined by dividing lowmax by midmax of each snoring event and averaging. High_Low_Max_Ratio is determined by dividing lowmax by himax of each snoring event and averaging. High_Mid_Max_Ratio is determined by dividing midmax by himax of each snoring event and averaging. High_Mid_Max_Ratio is determined by dividing himax by midmax of each snoring event and averaging.

Following determination of the initial set of template parameters, the 150 breathing events are evaluated using the snore template. The results are then used to adjust the breathing parameters of the snore template based upon the number of errors. To evaluate the snore template, a presumption is first made that each of the 150 events is a breath. The breath parameters of the snore template are then applied along with the set of determined values for each breath within a set of inequalities to classify each event as either snoring or breathing. In applying the snore template, the first parameter, Low_High_Dense_Ratio is multiplied by hdensl of an event of the 150 events and the product compared to ldensl. If ldensl is greater than the product, the breathing event is a snore. Likewise, Low_High_Max_Ratio is multiplied by himax of the event and if the product is less than lowmax the event is a snore. Low_Mid_Dense_Ratio and High_Mid_Dense_Ratio are each multiplied by mdensl and if both products are less than ldensl, then the event is a snore. Both Low_Mid_Max_Ratio and High_Mid_Max_Ratio are multiplied by midmax and if the first product is less than lowmax and the second product is less then himax, then the event is a snore. As one final test of the event, and as a fail-safe check, High_Low_Max_Ratio and High_Mid_Max_Ratio are each multiplied by himax and where the first product is greater than lowmax and the second product is greater than midmax, then the event, in all cases, is assumed to be a breath. As another final test, the system tests whether the event was strongly classified as a snore (e.g., the snore index=1 or 2) or a wheeze (e.g., the snore index=4 or 5). If so, the event is a snore.

Following evaluation of the 150 breathing events using the preliminary breath parameters, a comparison is made between the evaluation under the template and original manual analysis. If the manual analysis agrees with the analysis under the 6 preliminary breath parameters of the template, then the analysis is extended to the remaining (3,500–150) events. If the manual analysis does not agree with the analysis under the template by some threshold (>5%) then the system enters an iterative phase to facilitate convergence of the preliminary breath parameters to a state where the number of snores detected by manual analysis and template agree. To facilitate convergence the system sequentially varies each breath parameter by some factor (e.g., 5%) one step at a time to a maximum and minimum value while holding the other breath parameters constant. After each change, the system again evaluates each of the 150 events and compares the analysis under the template with the analysis under the manual analysis. After the iterative analysis is complete, the system selects the set of breath parameters providing the best "fit" (most events agree). If the difference in correlation between the analysis under the template and manual analysis is less than some threshold value (<5%) the analysis is extended to the remaining (3,500–150) breath events.

If the difference is not less than the threshold value, then a second set of 150 events are selected for manual analysis. The additional 150 events are manually analyzed in a manner similar to the first 150 events and then added to the first group to provide a set of 300 events. The system evaluates the 300 events using the breath parameters produced as a result of the first set iterative steps. If the comparison between the number of snores produced by the template and manually analysis again exceeds the threshold, the system again iteratively adjusts the breath parameters by sequentially adjusting each breath parameter one step at a time between a minimum and maximum value while holding the other parameters constant. At the end of the iteration, a new set of adjusted breath parameters are produced. The new set of adjusted parameters are then used to compare snores under the template and manual analysis. If the difference is below the threshold (or if the operator decides that convergence is adequate), then the remaining events (3,500–300) are evaluated using the new template, otherwise the process is repeated.

Under the embodiment, the events determined as snoring by the iterative process are ordered according to amplitude. Following ordering, the snores are grouped, starting with the largest of the ordered snores, based upon a previously determined snore index and upon the percent of velum snores (snore index of 1 or 2) within the group. The grouping process is stopped where the group contains no more than 85% velum snores. The amplitude ratio between largest and smallest snores is determined. The amplitude ratio between the largest and smallest snores is determined and set equal to the amplitude distribution index.

Following the automatic scoring of snoring events after convergence, the system can be used to generate an error matrix of snore indicia comparing automatic and manual analysis. Because of the complexity of automatic assignment of a snore index to a snore, a group of 50 snores that were automatically assigned a snore index of 2 may be determined by manually analysis to, in reality, be comprised of 10 index 1, 35 index 2 and 5 index 3 snores. Under the embodiment, once convergence is achieved, a new respiratory event set (i.e., 150 events) is selected (of the 3500 events) and again manually analyzed. The manual and automatic scores of the 150 events are then compared and used to produce an error matrix. The horizontal axis of the matrix is labeled with snore indexes of from 1 to 5, wheeze or artifact identified through manual analysis. The vertical axis is labeled with snore indexes of from 1 to 5, wheeze or artifact identified through automatic analysis. Each event of the 150 manually analyzed respiratory events is placed within the matrix using the automatic and manual snore indexes. Events which produced identical results under both automatic analysis and manual analysis are placed along a diagonal. Events placed off the diagonal, indicating a mismatch between automatic and manual ae and abscissa values of respective evaluations.

The error matrix, offering a comparison of automatic analysis versus manual analysis for the same breathing events, provides a means of evaluating the effectiveness of automatic analysis. The error matrix may also provide a means of manually adjusting a distribution of index values among classifications in such a manner as to more accurately reflect the results of the manual analysis. In the above example, if the total events of 500 out of 3500 events were automatically scored as index 2, the program will correct the results using the error matrix by assuming that only 350 are truly index 2, while 100 are actually index 1, and 50 are assumed to be index 3.

Under an embodiment of the invention, the ability to measure and compare snoring loudness both before and after UPPP (or LAUP) is very important. Comparing loudness from a microphone recording from two different recording sessions, on the other hand, is not very reliable, since the microphone is influenced not only by the snoring loudness, but also by the cannula, patient position, microphone orientation, etc.

To overcome the difficulties of comparing loudness, a new value (i.e., relative snoring loudness) is defined, which is for the most part, independent of the vagaries of microphone use. Relative snoring loudness is defined as the snore loudness compared to the average loudness of the breath events recorded during sleep. The loudness of a breath event in absolute terms can be defined, for example, by evaluation of the expression, "20 log (maximum amplitude of the FFT components of the event marked as a breath)". The relative snore loudness can be defined by the expression, "20 log (AS/BS)", where AS is the maximum amplitude of the snore FFT components and AB is the average amplitude of the FFT components over all of the events marked as ordinary breaths (or the neighboring breaths).

In another embodiment of the invention, the classifications of sleep disorders discussed above may be used to generate a qualitative measure of breathing resistance during sleep. Such a measure may include a breathing resistance index, an apnea index, etc. Such measures may be useful not only as an indication of the severity of a particular type of sleep disorder but as a screening tool for long-term health problems (e.g., heart problems, high blood pressure, risk of stroke, etc.).

Breathing resistance, as such term is used herein, may be determined on a relative basis. Normal breaths, as described above, are determined by comparison of breathing events with breath thresholds or via listening (i.e. operation can listen to an event and decide whether its breathing into. Other high resistance breathing events (e.g., snoring, strider, wheezing, apnea, hypopnea, artifacts, etc.) are determined by loudness and a frequency content and duration of the event. These high resistance events are respiratory events other than effortless breathing.

Under one embodiment, the index of resistance may be expressed as either a ratio of normal breaths to breaths involving resistance to breathing (e.g., snoring, hypopnea, wheezing) over a time period or as a resistance value for each breath. Where the index of resistance is expressed as a ratio (herein referred to as a breathing resistance occurrence index, or BROI), the ratio may be expressed by the equality as follows:

$$BROI = (N_S \times 100)/(N_S + N_B),$$

where $N_B$ are the number of normal breathing events (as discussed above) and $N_S$ is the sum of all other higher resistance events (e.g., snore scores 1–5, and optionally apnea, hypopnea, wheezing, etc.). Evaluation of $N_B$ and $N_S$ may be accomplished manually, statistically, or automatically using FFT evaluation.

Where the index of breathing resistance is expressed as an absolute value, R, it may be directly related to loudness by the equality as follows:

$$R = Am + R_o,$$

where $R_o$ is an average loudness of a normal breath, L is the loudness of a specific event, m is an event type (e.g., snore score 1–5, apnea, hypopnea, wheezing, artifact, etc.), and A is a coefficient specific to the event type. An average breathing resistance index can be obtained by adding the R value for each event during an interval and dividing by the number of events.

As each value of R is calculated for each event, it may be displayed immediately or stored for later retrieval. Storage of R values may be sequential in time or based upon a set of highest values.

Where the index of breathing resistance is expressed as a ratio in the form of BROI, an evaluator is given an indication of the pervasiveness of sleep respiratory problems by the value given for BROI. In comparison, the absolute value, R, gives an evaluator an indication of the severity of individual respiratory events.

Further, while an evaluator may look at the BROI over an entire night (or over short periods) as an indication of the severity of the problem, the evaluator may also examine the resistance of individual respiratory events (i.e., R values) over a shorter time period as a means of evaluating a risk to a patient over those episodes. To do so, the evaluator may call up a series of events for display on a bar chart of R values displayed on the computer terminal 30. The evaluator may scroll forwards or backwards over a display interval to further evaluate the severity of an episode.

A further evaluation of sleep disorders based upon the above identification of respiratory events can be made using an index of maximum apnea density. The maximum apnea density index may be determined by identifying a most dense interval of apnea within the monitored respiratory sound and then calculating the number of incidents per unit of time (e.g., minute). Thus, for example, a time interval is selected (e.g., 15 min./.25 hours, etc.), and the interval with the most apnea events is then identified and the number of apnea events summed to obtain a total number of apnea events for the interval. The total number of apnea events during terval (e.g., in hours) to provide an index of maximum apnea density (e.g. in events per hour). Similarly, an hypopnea density index can be obtained by identifying the interval with the most incidents of hypopnea, and then dividing the total number of hypopnea events by the interval length (e.g., hours). A maximum respiratory disturbance density (MRD) can be obtained by summing the apnea and hypopnea events within the time interval to thereby obtain a total. This total may then be divided by the length of the time interval to obtain a respiratory disturbance index.

The foregoing specification describes only the preferred embodiments of the inventions as shown. Other embodiments besides the ones described above may be articulated as well. The terms and expressions, therefore, serve only to describe the invention by example only and not to limit the invention. It is expected that others will perceive differences which, while differing from the foregoing, do not depart from the spirit and scope of the invention herein described and claimed.

What is claimed is:

1. A method of determining a maximum apnea density index of a sleeping subject from a set of respiratory sounds from the subject comprising the steps of:

selecting a set of respiratory events of the set of respiratory sounds;

determining a maximum apnea density index by identifying a time interval of predetermined duration within the set of respiratory events which has a maximum number of apnea events and determining the maximum apnea density index based upon the number of apnea events in that time interval.

2. A method of determining a maximum hypoapnea density index of a sleeping subject from a set of respiratory sounds from the subject comprising the steps of:

selecting a set of respiratory events of the set of respiratory sounds;

identifying a time interval of predetermined duration within the set of respiratory events which has a maximum number of hypoapnea events, and determining the maximum hypoapnea density index based upon the number of hypoapnea events in that time interval.

3. A method of determining a qualitative breathing resistance index of a sleeping subject from a set of respiratory sounds from the subject comprising the steps of:

selecting a set of respiratory events of the set of respiratory sounds;

determining a classification content of the set of respiratory events; and determining a qualitative breathing resistance index based upon the classification content of at least a portion of the set of respiratory events including determining an average loudness for normal breathing events in the set of respiratory events, and the loudness of a specific event, and then calculating an absolute index based upon the average loudness and specific loudness.

4. The method of claim 3, wherein the step of determining a classification content further comprises the step of visually scanning a graphical representation of the breathing events.

5. The method of claim 4 further comprising the step of listening to respiratory events selected based upon the visual scan and classifying the respiratory event based upon the audio sound of the respiratory event.

6. A method of determining a qualitative breathing resistance index of a sleeping subject from a set of respiratory sounds from the subject comprising the steps of:

selecting a set of respiratory events of the set of respiratory sounds;

determining a classification content of the set of respiratory events including classifying at least some of the respiratory sounds of the set of respiratory events as high resistance respiratory events; and determining a qualitative breathing resistance index based upon the classification content of at least a portion of the set of respiratory events including calculating a ratio of the number of breaths involving high resistance to breathing to a sum of all breathing events.

7. A method of determining a relative breathing resistance index of a sleeping subject from a set of respiratory sounds from the subject comprising the steps of:

selecting a set of respiratory events of the set of respiratory sounds;

determining a classification content of the set of respiratory events including classifying at least some of the respiratory sounds of the set of respiratory events as high resistance respiratory events and determining a total number of breathing events and a total number of the breathing events that are snoring events in the set of respiratory events; and determining the relative breathing resistance index based upon the total breathing events and total snoring events.

8. The method of claim 7, wherein determining the qualitative breathing resistance index comprises determining a ratio of total high resistance breathing events to total breathing events.

9. A method of determining a respiratory disturbance index of a sleeping subject from a set of respiratory sounds from the subject comprising the steps of:

selecting a set of respiratory events of the set of respiratory sounds;

determining a classification content of the set of respiratory events; and determining the respiratory disturbance index by summing all apnea events and all hypoapnea events occurring during a time-interval and determining the respiratory disturbance index based upon the sum.

10. A method of determining a qualitative breathing resistance index of a sleeping subject from a set of respiratory sounds from the subject comprising the steps of:

selecting a set of respiratory events of the set of respiratory sounds;

determining a classification content of the set of respiratory events;

determining a qualitative breathing resistance index based upon the classification content of at least a portion of the set of respiratory events;

classifying at least some of the respiratory sounds of the set of respiratory events as high resistance respiratory events; and determining a percentage of snoring events dominated by a velum-like pattern by tabulating the snoring events of the classified respiratory event set characterized as velum-like; dividing by the total number of snoring events in the respiratory event set; and multiplying by one hundred.

11. The method of claim 10, further comprising the step of classifying at least some of the respiratory sounds of the set of respiratory events as apnea.

12. A method of determining a qualitative breathing resistance index of a sleeping subject from a set of respiratory sounds from the subject comprising the steps of:

selecting a set of respiratory events of the set of respiratory sounds;

determining a classification content of the set of respiratory events;

determining a qualitative breathing resistance index based upon the classification content of at least a portion of the set of respiratory events;

classifying at least some of the respiratory sounds of the set of respiratory events as high resistance respiratory events; and determining a percentage of breathing events having at least some velum-like patterns by tabulating breathing events classified as a velum snore; dividing by the total number of breathing events in the respiratory event set; and multiplying by one hundred.

13. The method of claim 12, wherein the step of determining a classification content is based upon analysis of the respiratory sounds only.

14. The method of claim 12, wherein the step of selecting comprises listening to the set of respiratory sounds and manually selecting the set of respiratory events.

15. The method of claim 12, wherein the step of determining a classification is performed automatically using dynamically calculated classification parameters.

16. The method of claim 12, wherein at least a portion of the set of respiratory sounds are recorded and the recorded set of respiratory sounds are used in the step of determining the classification content.

* * * * *